United States Patent
Unlu et al.

(10) Patent No.: US 7,695,680 B2
(45) Date of Patent: Apr. 13, 2010

(54) RESONANT CAVITY BIOSENSOR

(75) Inventors: M. Selim Unlu, Jamaica Plain, MA (US); David A. Bergstein, Allston, MA (US); Michael F. Ruane, Brookline, MA (US); Bennett B. Goldberg, Newton, MA (US)

(73) Assignee: The Trustees of Boston University, Boston, MA (US)

( * ) Notice: Subject to any disclaimer, the term of this patent is extended or adjusted under 35 U.S.C. 154(b) by 936 days.

(21) Appl. No.: 10/549,991

(22) PCT Filed: Mar. 19, 2004

(86) PCT No.: PCT/US2004/008558

§ 371 (c)(1),
(2), (4) Date: Sep. 19, 2005

(87) PCT Pub. No.: WO2004/083820

PCT Pub. Date: Sep. 30, 2004

(65) Prior Publication Data

US 2006/0182659 A1 Aug. 17, 2006

Related U.S. Application Data

(60) Provisional application No. 60/455,970, filed on Mar. 19, 2003.

(51) Int. Cl.
*G01N 21/00* (2006.01)
*G01N 21/03* (2006.01)
*G02B 6/00* (2006.01)
*G01N 21/41* (2006.01)
*G01N 33/53* (2006.01)

(52) U.S. Cl. ............ 422/82.05; 422/82.06; 422/82.07; 422/82.08; 422/82.09; 422/82.11; 435/7.1; 356/136; 356/454; 356/480; 356/519; 436/164; 436/165; 385/12

(58) Field of Classification Search .................. None
See application file for complete search history.

(56) References Cited

U.S. PATENT DOCUMENTS

| | | | |
|---|---|---|---|
| 4,857,273 A | 8/1989 | Stewart | 422/68 |
| 4,917,462 A * | 4/1990 | Lewis et al. | 359/368 |
| 5,640,237 A | 6/1997 | Esrig et al. | 356/237 |
| 5,851,488 A * | 12/1998 | Saul et al. | 422/67 |
| 5,982,534 A | 11/1999 | Pinkel et al. | 359/387 |
| 6,143,247 A | 11/2000 | Sheppard, Jr. et al. | 422/63 |
| 6,287,874 B1 | 9/2001 | Hefti | 436/501 |
| 2002/0068018 A1* | 6/2002 | Pepper et al. | 422/82.05 |

* cited by examiner

*Primary Examiner*—Jill Warden
*Assistant Examiner*—Neil Turk
(74) *Attorney, Agent, or Firm*—Weingarten, Schurgin, Gagnebin & Lebovici LLP

(57) ABSTRACT

An assay system having a channel bounded by first and second reflective surfaces adapted to accommodate a fluid material therebetween and defining a plurality of regions in an array between those surfaces with each region defining a resonant cavity and adapted to receive a capturing material on a surface thereof whereby a source of radiation illuminates each region to provide a standing wave of radiation of within the cavity indicative of binding of said capturing agent to material under investigation, a binding thereof being detected in response to radiation from each cavity indicative of a change in the standing wave pattern.

41 Claims, 12 Drawing Sheets

RESONANT CAVITY BIOSENSOR

CROSS REFERENCE TO RELATED APPLICATIONS

This application claims priority to commonly assigned Provisional Application Ser. No. 60/455,970 filed Mar. 19, 2003 and International Patent Application Number PCT US2004/008558 filed on Mar. 19, 2004. International Application No. PCT/US00/12287, filed 5 May 2000 is incorporated herein by reference.

STATEMENT REGARDING FEDERALLY SPONSORED RESEARCH OR DEVELOPMENT

N/A

BACKGROUND OF THE INVENTION

In bio-research, ecological testing, medical testing, drug testing and bio-weapon and hazards detections there is a need for rapid, simultaneous and real time detection of various agents. Typically the agents are provided in a fluid to a test structure, generally an array of some form in which capturing materials of diverse types capable of binding to one or more of the materials undergoing test and provided in the fluid medium. The binding is a result of an affinity that molecules or bio-molecules have for each other and includes the affinities of DNA, RNA, proteins, small molecules and other molecules. DNA arrays and protein arrays, commonly called DNA or protein chips, are two technologies used for bio-molecule affinity sensing in such fields as genomics and proteomics.

The array of capturing materials is created in a known pattern such that by correlation of the binding response of the capturing material to the fluid born molecules under test, it is possible by detecting the level of binding at each array element to determine what materials under test are present. In one case of DNA or RNA testing, various sequences of the DNA or RNA molecule are affixed to corresponding locations in the array. DNA or RNA in the fluid being tested will tend to bind where the sequences therein strongly match the sequences attached to the various array sites.

Test methods known to date fail to provide high throughput, real time operations or to avoid difficult labeling processes, or to avoid capturing material incompatibility with metal sensor surface, requiring cumbersome linking chemistry that may adversely affect binding properties.

Among the techniques previously used which fail to provide all of these requirements in combination are fluorescent tagging. Fluorescent tagging procedures suffer from a number of problems including the difficulty of tagging and the possibility of tagging altering the binding properties. Moreover tagging procedures are difficult to monitor continuously in real time. Among other techniques surface plasmon resonance is popular. This technique, however, requires the affixation of molecules to a metal surface, particularly gold, which has the above mentioned incompatibility problem. Other techniques include waveguide techniques and acoustic detection techniques. Neither of these accommodates a high throughput, requiring a large number of array elements.

Finally, another known technique, reflectometric interference spectroscopy, suffers from the complication of using multiple fiber probes, which greatly hinders its ability to become high throughput.

BRIEF SUMMARY OF THE INVENTION

The present invention provides an affinity detection system which has high throughput, is real time and avoids the complexities of metal, cumbersome equipment and other deficiencies of prior art techniques.

According to the teaching of the present invention, an array of biosensor or capturing material elements is formed between first and second surfaces of reflective mirrors. Typically, the mirrors are formed by multi-layer dielectric surfaces selected to be reflective at a particular range of wavelengths, commonly in the IR frequency regions. Light, typically from a laser, is applied through the array and focused onto a photo-detection system such as a CCD chip or photodetector array where each element of the capturing array is focused onto one or more pixels of the image chip.

A fluid containing materials under test flows through the array between the surfaces forming the mirror elements, the material having an affinity for a capturing material in one or more array cells. Instead of a fluid (gas or liquid with particles or fluid components under test) a solid of appropriate transparency may be tested. These materials will be bound to the capturing material of that cell having such an affinity changing the resonant properties of the resonant cavity formed between the mirror surfaces in that cell. The result will be a change in the light received by the corresponding CCD pixels. That change can be detected by processing electronics correlating the position of the change, its nature and the known affinity of that particular resonant cavity cell.

In this fashion, a large number of bio-molecules or other molecules can be tested for in real time. Array dimensions of hundreds of thousands or millions of cells are possible and the processing electronics available today can easily provide a real time indication of the nature of molecules present in a medium being tested.

BRIEF DESCRIPTION OF THE SEVERAL VIEWS OF THE DRAWINGS

These and other features of the present invention are described in the following detailed description taken in conjunction with the drawing of which.

DETAILED DESCRIPTION OF THE INVENTION

Figure 1:
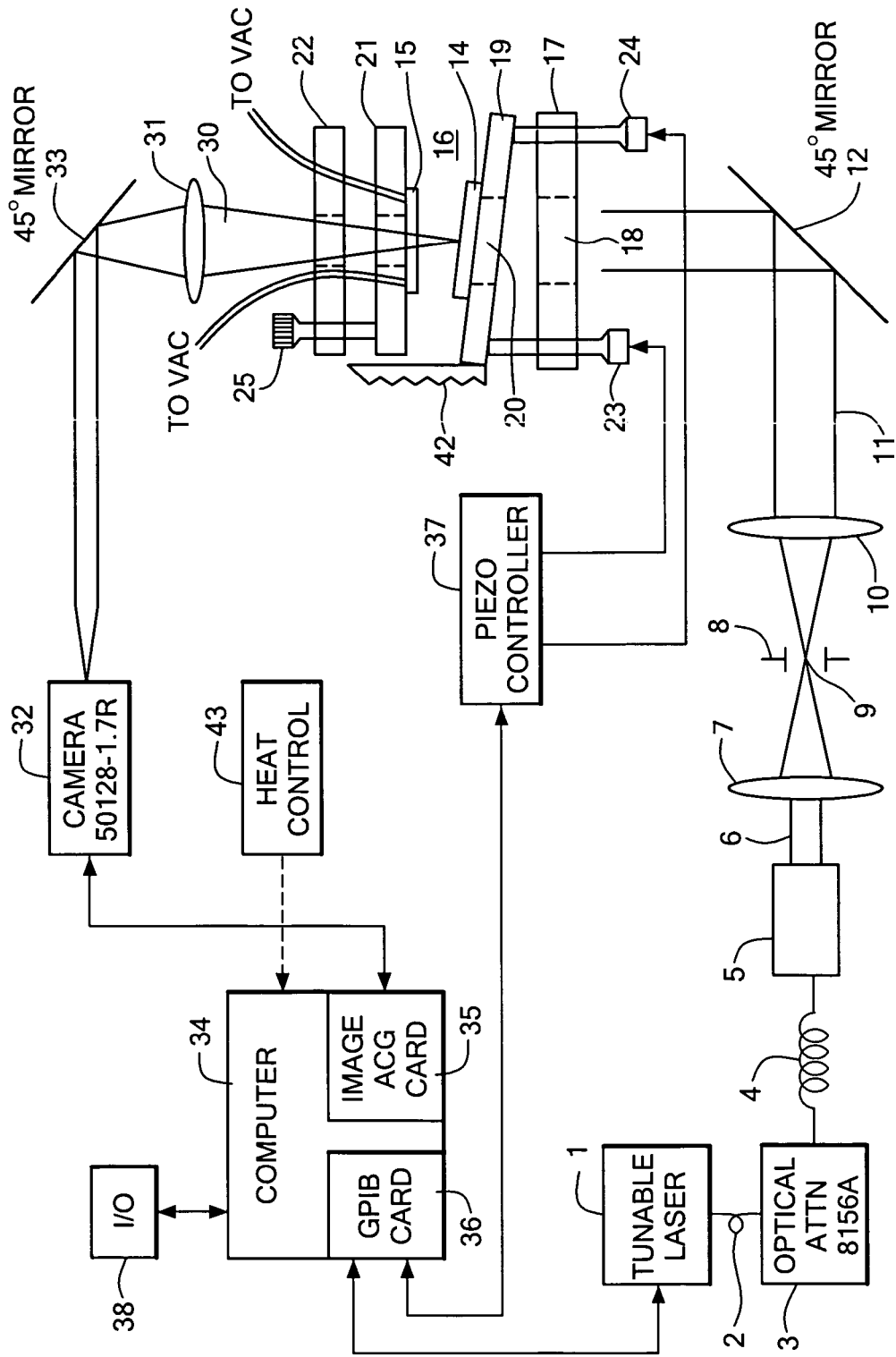
FIG. 1 is a diagram illustrating the components of a testing system of the present invention.

FIG. 1 illustrates an optical control system according to the invention in which a wavelength tunable laser 1, which may be an Aristu MNG638A provides output radiation typically in the vicinity of 1560 nanometers (15,600 Angstroms) to a single mode optical fiber 2. Radiation in the fiber 2 is applied to an optical attenuator 3, which may be an Agilent 85156A. The attenuator provides dynamic adjustment consistency to promote the operation of the system as a whole as described below. In order to provide beam cleaning which insures a Gaussian distribution to the spatial intensity profile of the beam, the output of the attenuator 3 is applied through a long coil of single mode fiber 4, typically 5 Km. The thus cleaned light is applied through a fiber collimator 5 which uses an antireflective coated objective at 1550 nanometers. The collimator produces a 1 mm beam, the diameter being measured between half maximum intensity points.

The collimated beam 6 is applied to an optical system comprising a lens 7 which is in the exemplary example a 15 mm focal length antireflective coated lens. The converging beam from the lens 7 is applied through a 50 micron aperture 8 placed at the focal point 9 of the beam from the lens 7. The function of the 50 micron aperture is to provide further beam cleaning. The thus clean beam is applied to a further antireflective coated lens 10, typically of a 125 mm focal length. The lens 10 produces a collimated beam 11, in this example of 10 mm width between half maximum intensity points. The beam 11 is reflected at right angles by a 45° mirror 12 into the array of cells. This optical system may be a microscope system.

The detection system comprises a cavity 16 formed between first and second reflecting surfaces 14 and 15 separated by a space within which a standing wave is generated by the radiation in beam 11. That radiation is applied through a lower support 17, aperture 18 into a lower or first stage 19 through a further aperture 20.

The second reflective surface 15 is supported by a second stage 21 supported by a second support 22. Adjusters 23 and 24 allow adjustment of the first stage 19 with respect to the first support 17 while a micrometer 25 provides a similar function for the second stage 21 with respect to the support 22.

The light in beam 11 creates a standing wave pattern in the cavity 16, particularly one dependent upon the characteristics of a capturing material applied to each cell in an array on the mirror 14, all as described more completely herein below. Light of an intensity dependant upon the degree of resonance within each cell travels in a beam 30 through a focusing lens 31 to a camera 32, typically by reflection from a 45° mirror 33. The camera 32, which may be a Sensors Unlimited SU128-1.7R camera having a InGaAs sensor with pixels in a 128×128 array, receives that light. Typically, each cell will be imaged onto one or more pixels in the array of camera 32. The image from camera 32 is read into a computer 34 to an image acquisition card 35, which may typically be a National Instrument NI-PCI1422. The computer 34 has a controller card 36, typically a GPIB card, which applies control signals to the tunable laser 1. The card 36 also operates through a piezoelectric controller 37 to control piezoelectric actuators on the adjusters 23 and 24, typically placed at their tips where they join the first stage 19. The computer 34 may have an input/output interface 38 for communication with users, networks, printers display and other typical computer accessories.

The computer maintains a feedback loop through the piezoelectric controller 37 on the adjusters 23 and 24 via the camera 32 to sense fringe patterns in the optical image received and processed by the camera 32 which are an indication of an out of parallel condition between the stages 19 and 21, using known minimization techniques, the piezoelectric drives are operated to minimize those fringing elements thereby obtaining a parallel condition of the stages 19 and 21. The piezo elements are also operable by the computer to vary the spacing between reflectors as an alternative or complementary to wavelength scanning of the laser radiation.

A heating element 42 operates with a heat control unit 43 which may or may not have a connection to computer 34 in order to maintain or control the temperature between the stages 19 and 21 and in particular within the cavity region 16 where standing wave patterns are created by the incident illumination. This heat control accomplishes the function of avoiding dynamic changes on the mirrors during testing.

The computer 34 is programmed to process the image data from each pixel received by the camera 32 in order to determine the thickness between the reflectors 14 and 15 in each cell, representative of the binding of material flowed through the intermirror, cavity region 16 for biologic or chemical assay purposes. This process includes the steps of:

1. Low pass filtering the intensity wavelength response curves for each pixel with respect to wavelength;

2. Cross-correlating the local overlapping groups of pixels to find relative shifts in the intensity wavelength profile;

3. Solving an over-determined problem which involves integrating the shifts to find a consistent picture of capturing material surface thickness.

In order to develop an intensity wavelength response, the computer 34 will typically cause the tunable laser 1 to scan through a set of wavelengths.

In the operation of the feedback control of mirror alignment, if there is an angle between the two mirrors 14 and 15, such that the distance between them changes by more than a half wavelength, the cavity 16 will be resonant in some places and non-resonant at others. Everywhere the resonance condition is satisfied, the camera 32 and computer 34 will see bright spots on the camera monitoring transmission. For a perfectly flat mirror at an angle, this amounts to horizontal lines indicating equal cavity spacing where resonance is satisfied. As one of the angles is tuned, the lines grow closer together or farther apart. Closer together, indicates that the angle perpendicular to the lines is growing steeper. As one of the adjustment knobs is tuned far to one end, the lines will grow increasing close together and increasing perpendicular to that angle. If the same knob is turned the other direction, the lines grow closer and less perpendicular to that angle. As the knob is kept turning, the lines will go through an optimal position after which they will again start to grow closer together and more perpendicular to the direction of angle change. By adjusting very carefully, one can tune to that optimal position where the lines would start contracting again if there was movement in either direction of the tuning knob, and where the lines are actually parallel to the direction of the angle adjustment. This means that in this direction, the surface is completely flat. The same is repeated for the other direction. Once the other direction is done, the first one has probably moved a bit due to vibration from handling of the system, so an iterative approach may be needed to some extent. Wavelength changes move the lines but not their orientation, and the spacing between lines only changes slightly due to wavelength and can be taken into account by simply realizing that it was due to wavelength not angle change. Most often, we can not get to the point that the surface is completely lit due to surface curvature. A circle is eventually seen instead of the whole screen going bright, because the surface is curved and satisfying the resonant condition at only places on the circle, no matter how parallel the mirrors 14 and 15 are. When this circle is visible, the mirrors 14 and 15 are reasonably parallel and tuning can stop.

The peizo/computer control can take over this function and it allows much finer adjustment, making it easier to tune. The peizos do not disturb the system like the hand of a human operator on the adjusters 23 and 24 does. It is then possible to control the system to keep the mirrors 14 and 15 parallel throughout the operation of the biosensor.

Figure 2:
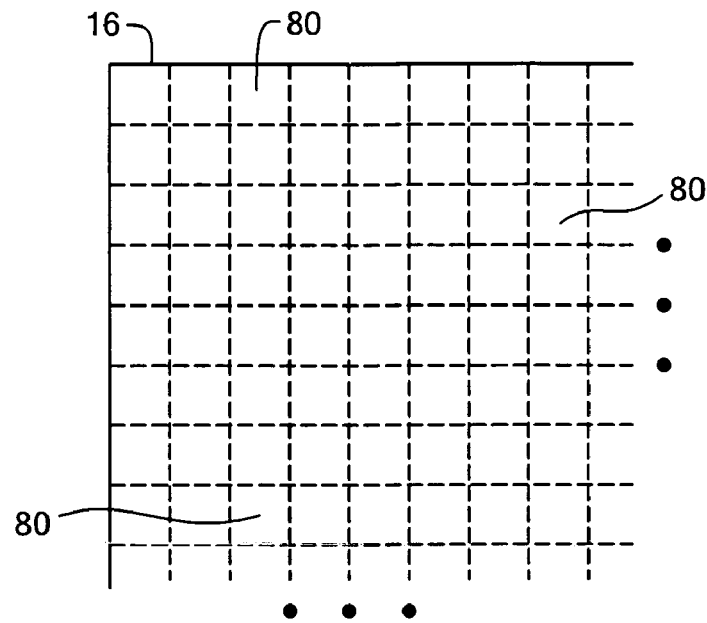
FIG. 2 illustrates an array of bio-probes according to the invention.
Figure 3:
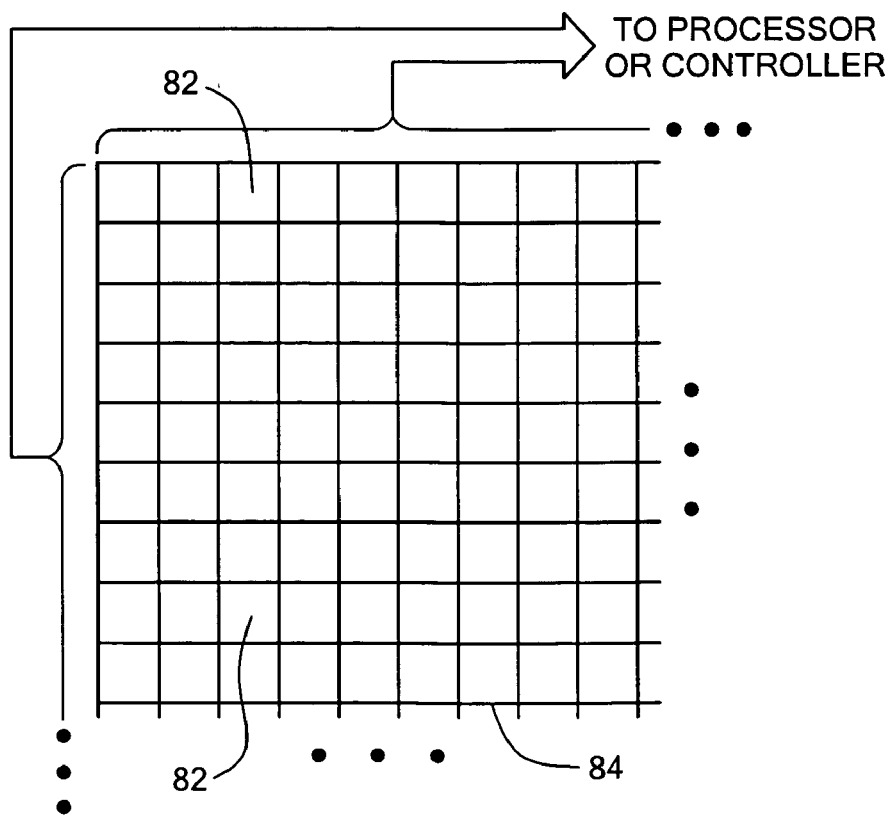
FIG. 3 illustrates an array of photo-detectors such as a photodetector array for use in the present invention or alternatively as a multi-cell light source according to an embodiment of the invention.

FIG. 2 illustrates an array of cells 80, typically those which may be applied to the surface of mirror 14 in bio or protein chips of known design. Hundreds of thousands or even millions of cells 80 can be provided in the mirror 14 within the cavity region 16. These cells 80, as noted above, are typically imaged into one or more pixels 82 of a photodetector array 84 in FIG. 3 within the multi-channel detector 30. Alternatively, the pattern illustrated by FIG. 3 can represent the pattern of light emitters such as from laser diodes. The memory associated with processor 34 will correlate one or more of the pixels 82 of the photodetector array 84 to corresponding cells 80 and the particular molecular affinity of the material bonded to the mirror 14, typically to several angstroms in depth.

Figure 4A:
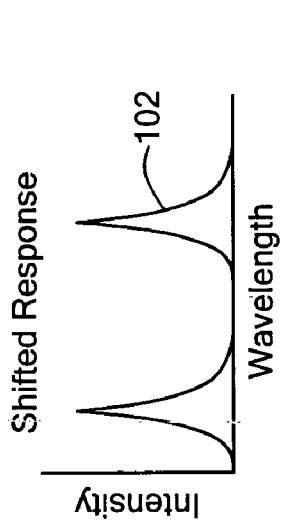
FIG. 4 illustrates the operation of a single cell in response to incident light according to the invention.
Figure 4B:
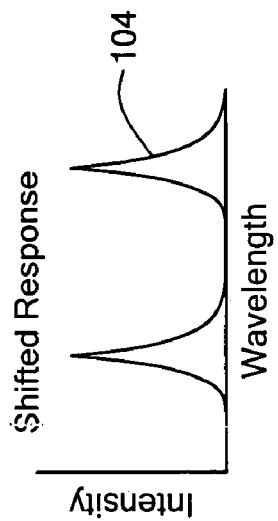
Figure 4:
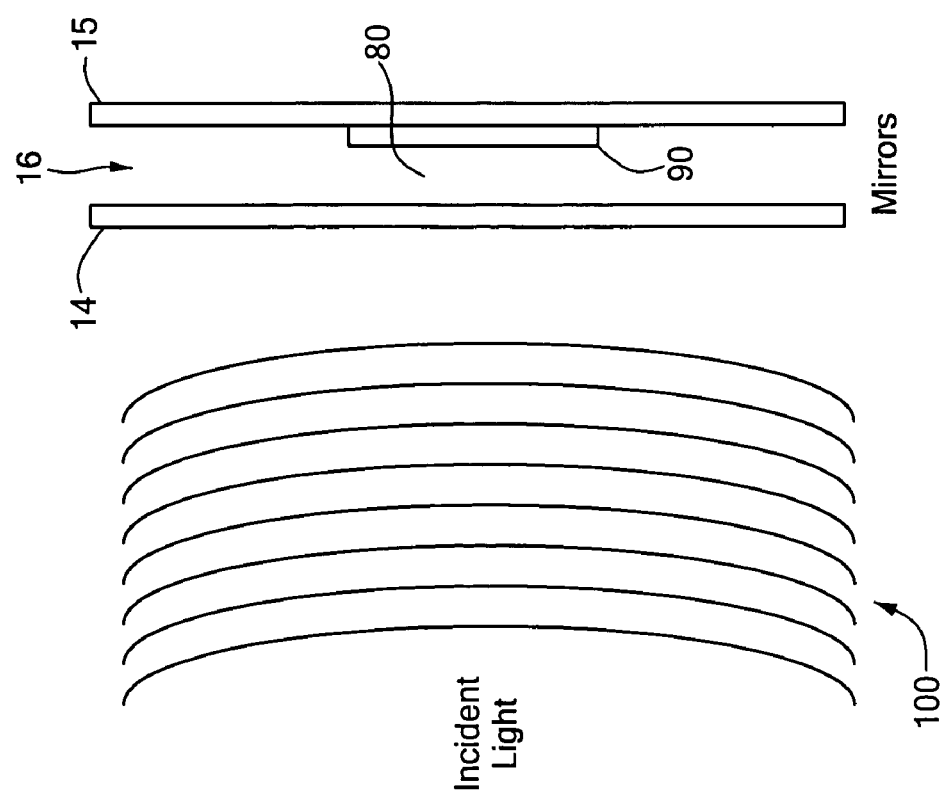

FIG. 4 illustrates diagrammatically the operation of a single cell 80 of the detection system of the present invention. The cell has a thin layer of a capturing material 90 affixed to it at each cell 80. The optical thickness of this material may be 5 angstroms and when binding occurs with molecules for which the capturing material there has an affinity the optical thickness may increase by as much as 10 angstroms.

Light from the laser 1 provides wavefronts 100 which pass into the cavity region 16 through mirror 12 and are reflective within the cavity 16 by the reflectance of the mirrors 14 and 15 to the wavelength and the incident radiation 100. As molecules in the flow through cavity 16 bind to the capturing material 90, the wavelength response will shift from an original array 102 in FIG. 4A to a shifted wavelength response 104 in FIG. 4B.

Figure 5:
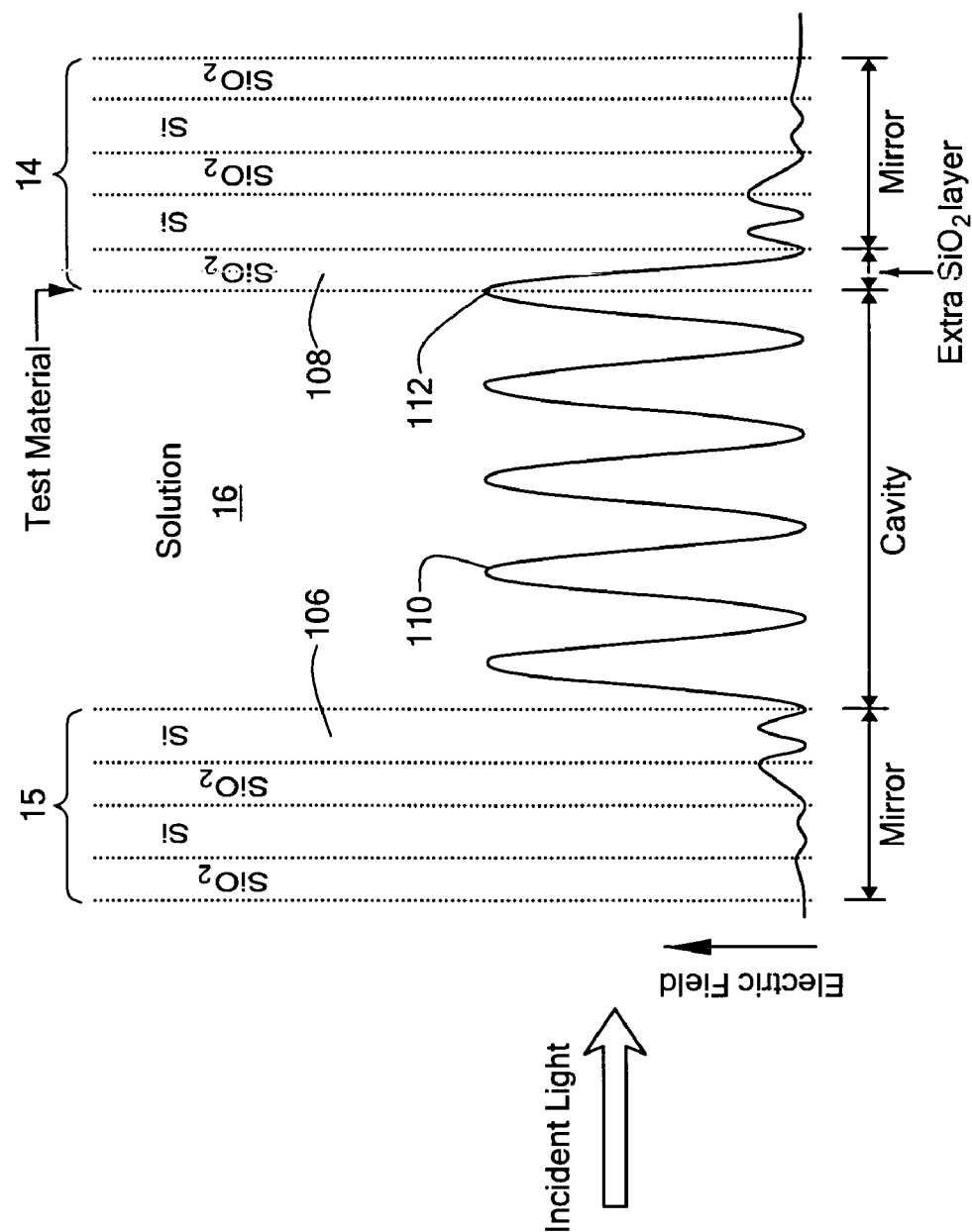
FIG. 5 illustrates a standing wave pattern typical of the present invention when exposed to illumination.

FIG. 5 illustrates in greater detail the mirrors 14 and 15 as consisting of a plurality of alternating silicon and silicon dioxide dielectric layers 106 and 108, respectively. As illustrated in FIG. 5, the surface of the first mirror 14 will typically be terminated with an extra silicon dioxide layer 108 causing a standing wave pattern 110 within the cavity region 16 illustrated in FIG. 5 to have a peak 112 at the outer wall of the layer 108. This maximizes the effectiveness and sensitivity of the detection system of the present invention.

Figure 6B:
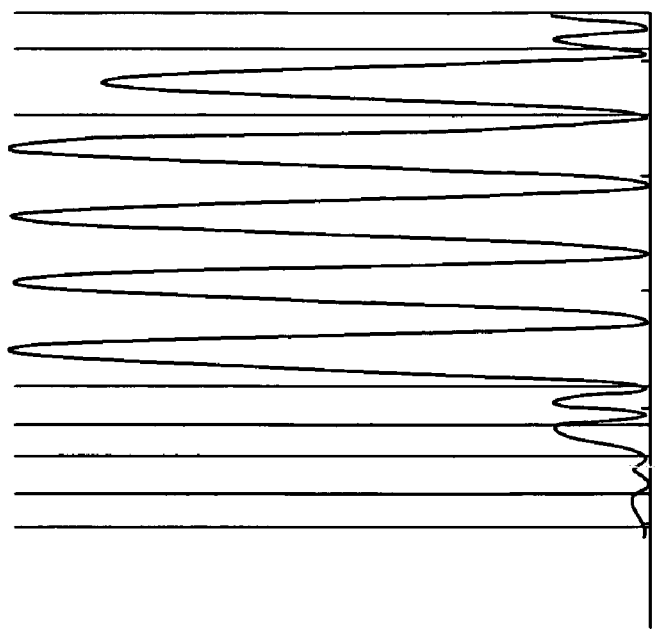
FIGS. 6A and 6B illustrate the variation in cell sensitivity as a function of dielectric layers in opposing mirrors according to the invention.
Figure 6A:
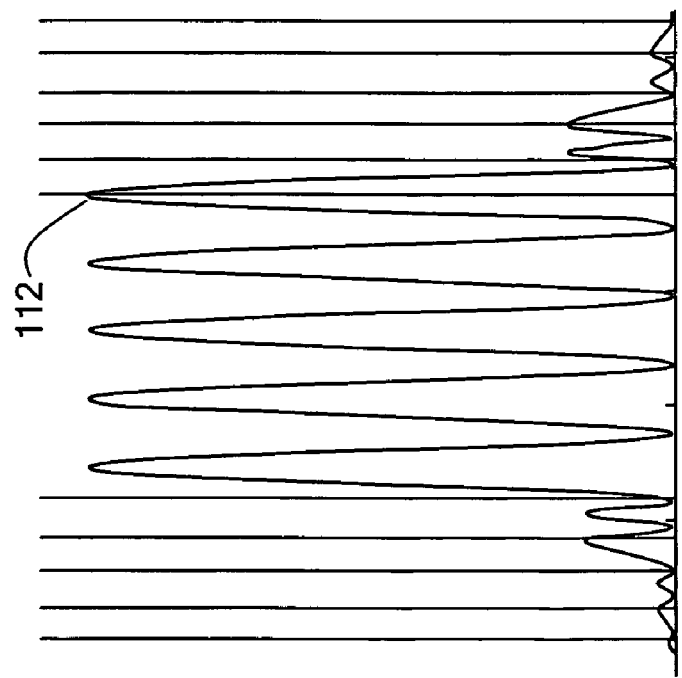
Figure 7B:
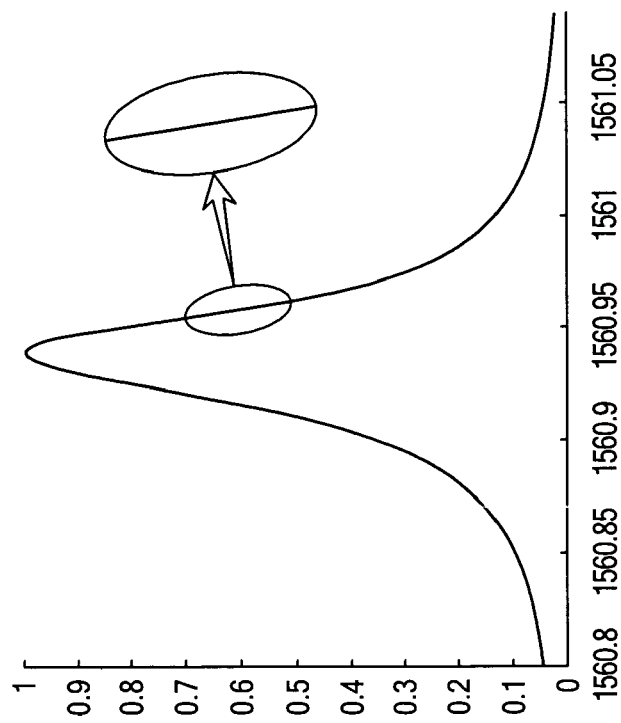
FIGS. 7A and 7B illustrate the change in resonant wavelength with the cavity narrowing from binding of molecules at different cavity dimensions and mirror compositions.
Figure 7A:
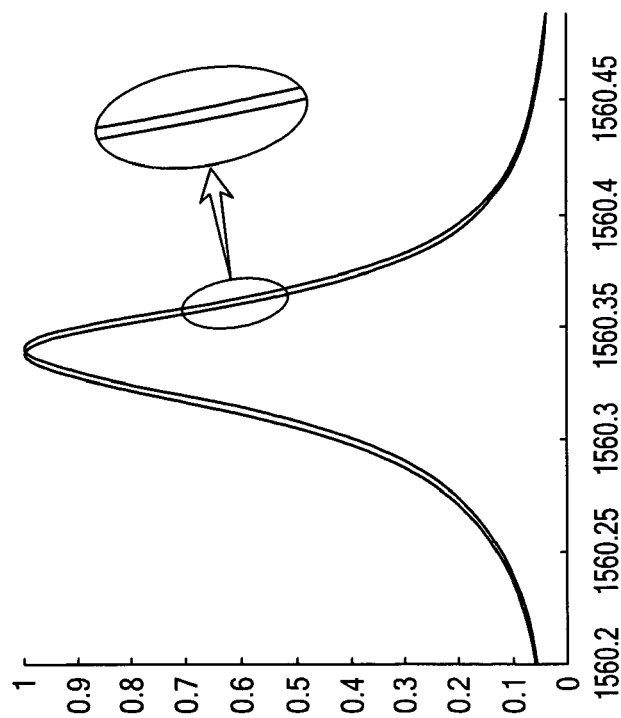

This effect is more clearly illustrated in FIGS. 6A and 6B and accompanying, corresponding FIGS. 7A and 7B. FIG. 6A illustrates substantially the standing wave pattern and dielectric layer scheme of FIG. 5. FIG. 7A illustrates the wavelength shift corresponding to a 5 nanometer buildup of material at the corresponding cell.

FIG. 6B illustrates the case where the standing wave pattern is a minimum at the front of the mirror 14 and the corresponding relatively insignificant change in resonant wavelength for a 5 nanometer buildup being illustrated in FIG. 7B.

In FIG. 7A:
 Cavity is 50 micron cavity filled with a buffer solution;
 Left curve is for 5 Angstroms of biomaterial;
 Right curve is for 10 Angstroms of biomaterial;
 270 nm extra SiO2 layer is present to maximize sensitivity;
 AR coating is present on mirror backsides;
 X-axis is wavelength in nm;
 Y-axis is transmission;
 Curves shifted 0.004 nm.

In FIG. 7B:
 Cavity is 50 micron cavity filled with a buffer solution;
 Left curve is for 5 Angstroms of biomaterial;
 Right curve is for 10 Angstroms of biomaterial;
 No extra SiO2 layer is present to maximize sensitivity;
 AR coating is present on mirror backsides;
 X-axis is wavelength in nm;
 Y-axis is transmission;
 Curves nearly indistinguishable; Curves shifted 0 nm.

Figure 8A:
FIGS. 8A, 8B and 8C illustrate the variation of cavity mirror transmittance as a function of wavelength with cavity mirror dielectric layer complexity.
Figure 8C:
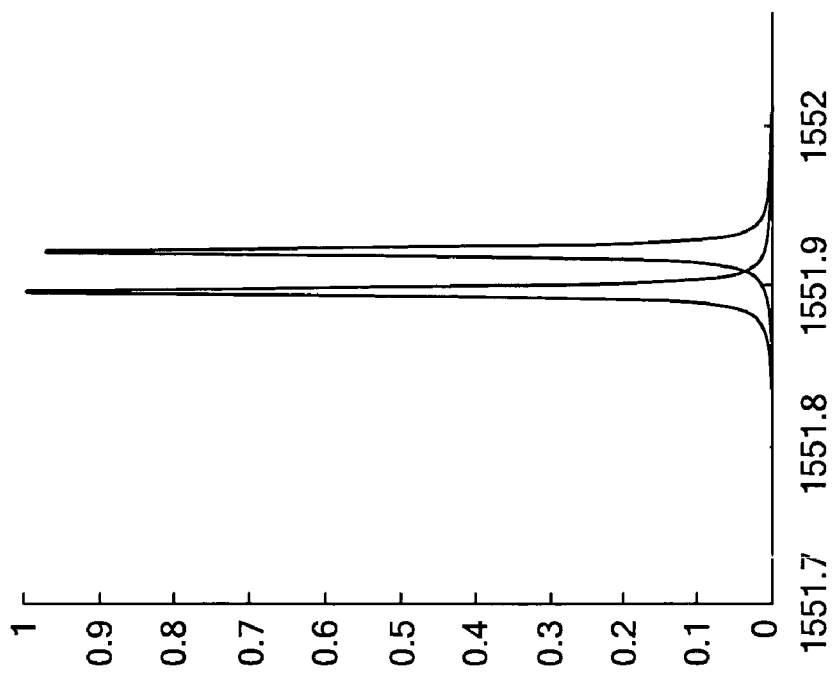
Figure 8B:
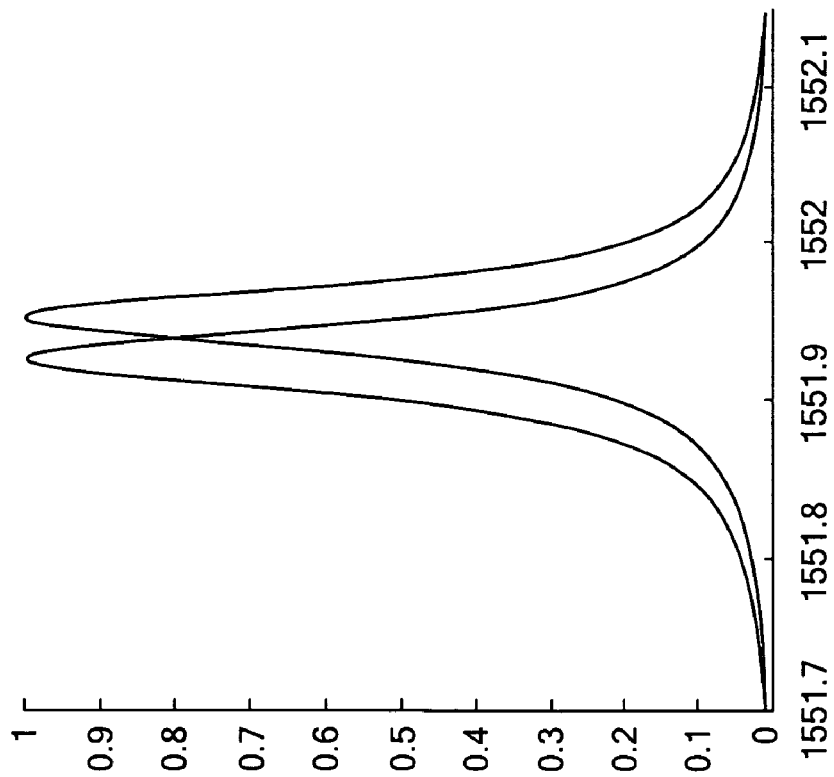

FIGS. 8A and 8C illustrate the sensitivity increase as the number of dielectric layers within the mirrors 15 and 14 increases essentially forming a Bragg reflector. FIGS. 8A-8B curves represent computer simulations corresponding, from left to right, to 2 sets of alternating high and low index layers, 3 sets, and 4 sets in the far right. The calculations use a solution index of refraction of 1.33 and the material is calculated with an index of refraction of 1.45. The capturing material layer is 0.05 nanometers while the target/capture layer thickness is 0.1 nanometers.

The embodiments of the invention may vary. In particular, the wavelength of the applied radiation may be other than within the infrared or IR bands, the radiation applied to the mirrors 15 and 14 may be other than orthogonal and the mirrors 15 and 14 may not necessarily be parallel. The processor and photodetector array, while typically measuring light amplitude as an indication of affinity binding, may detect phase, polarization or actual frequency shifts. The tuning of the laser 36 may be continuous or in discrete steps. A VCSEL array may alternatively be used as a source of radiation as well as laser diodes.

Simulation

Figure 9A:
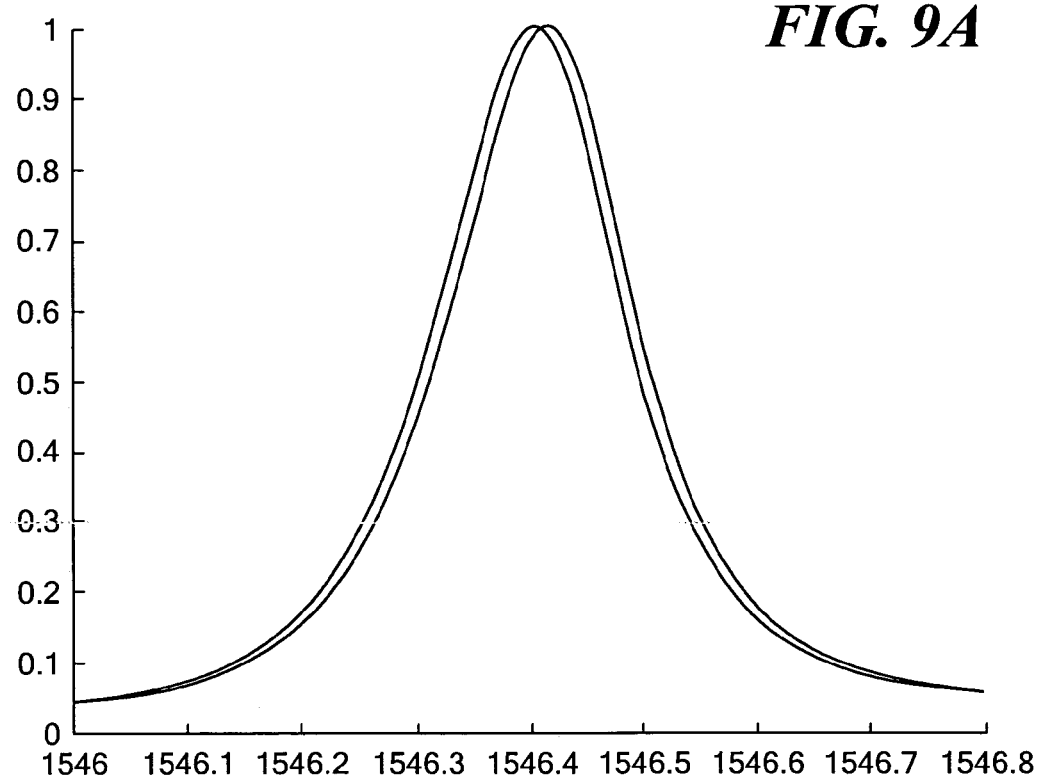
FIGS. 9A and 9B illustrate resonance under differing conditions useful in understanding the invention.
Figure 9B:
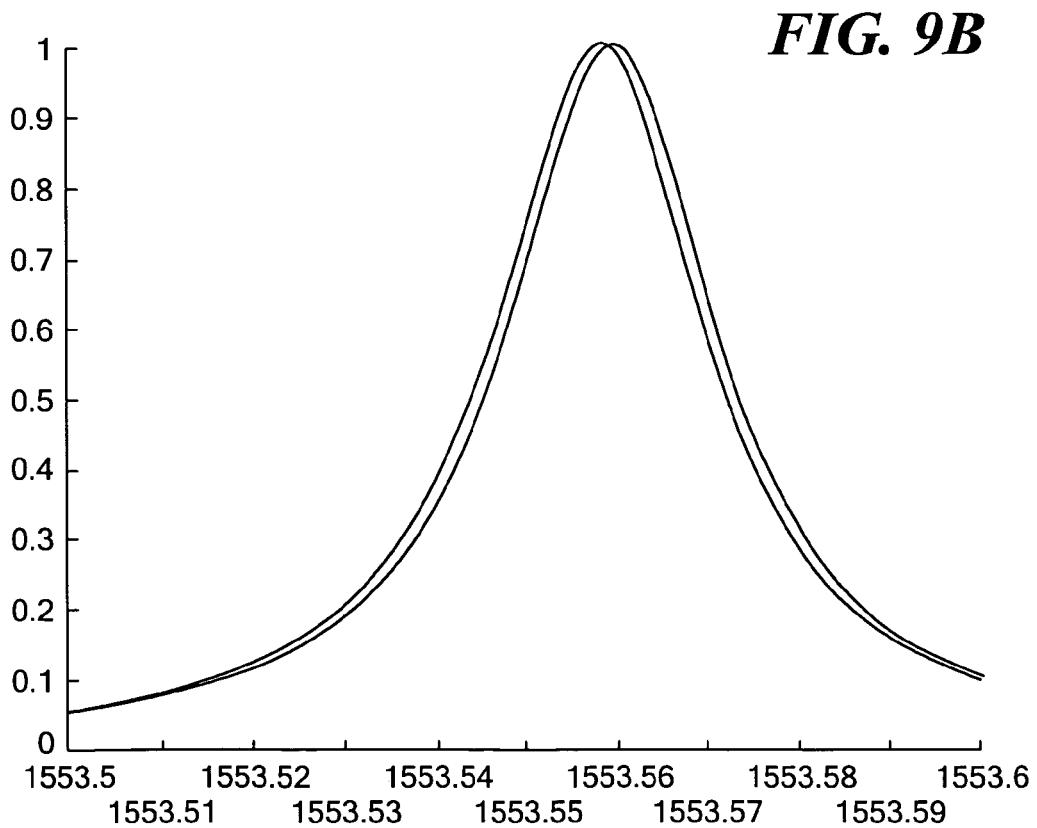

FIGS. 9A-9B show a simulation of wavelength shifts.
In FIG. 9A:
 Cavity is 10 micron cavity filled with a buffer solution;
 Left curve is for 5 Angstroms of biomaterial;
 Right curve is for 10 Angstroms of biomaterial;
 270 nm extra SiO2 layer is present to maximize sensitivity;
 AR coating is present on mirror backsides;
 X-axis is wavelength in nm;
 Y-axis is transmission;
 Curves shifted 0.012 nm.
In FIG. 9B:
 Cavity is 100 micron cavity filled with a buffer solution;
 Left curve is for 5 Angstroms of biomaterial;
 Right curve is for 10 Angstroms of biomaterial;
 270 nm extra SiO2 layer is present to maximize sensitivity;
 AR coating is present on mirror backsides;

X-axis is wavelength in nm;
Y-axis is transmission;
Curves shifted 0.001 nm.

EXAMPLE

Fabrication of test sample: A test pattern has been fabricated in SiO2 to test that the system is working (FIG. 10A). 270 nm of SiO2 was deposited on the top surface of the first reflector. This SiO2 layer serves to place the sensing surface at a position in the cavity where the field strength is high (approximately 1 quarter wavelength out from the reflector surface at the wavelengths we are scanning at). The SiO2 surface was then masked and lightly etched to leave 4 square features. The 4 squares are 50 μm×50 μm and 30 μm apart. The pattern is repeated every 500 μm. The sample was masked at the boxes and wet etched everywhere else using HF to remove approximately 15 nm of material. 4 boxes 50 μm×50 μm×15 nm should remain on top of 255 nm SiO2, on top of the reflector.

Running experiment: Micrometers were used to position the reflectors close to each other to form the cavity. A z-stage was used to translate one of the reflectors to approximately 100 μm away from the other, to form a 100 μm air cavity. Fringes could be seen on the video output from the camera, indicating that the reflectors were not parallel. An angle stage holding the other reflector was then carefully adjusted until the fringes could no longer be seen. Wavelength was scanned from 1545 nm to 1560 nm in 0.01 nm steps. An image of the cavity was captured at each step with approximately 6× magnification (FIGS. 10B and 10C out and in resonance).

Processing data: The resulting wavelength response curve for each pixel was then low pass filtered with a 5 samples/nm cutoff. The data were then broken down into groups of 9 waveforms taken from 3×3 sets of neighboring pixels. The groupings were made so that they overlap by 1 row or column of pixels with neighboring groups of 3×3. Within each 3×3 group, the 9 wavelength response curves were cross correlated to each other. The peak of the cross-correlations indicates the shift between those two waveforms. Nine (9) waveforms cross correlating with each other produces 81 correlations, including 9 auto correlations, which leads to 72 shifts describing the relative position of each pixel with respect to the other 8 pixels. This information is heavily redundant. A linear systems over determined problem is setup and solved to find 8 shifts for 8 of the pixels relative to the top left most pixel which was given the shift of zero. This was done for all of the overlapping groups of 3×3 pixels. The top left most group of 3×3 pixels was designated to have a zero overall offset. The offset of the other 3×3 groupings relative to this first 3×3 group was then determined. The offset for each of the 3×3 groupings was found from solving a linear systems over determined problem as well, where the equations are derived from the fact that the 3×3 groupings overlap by columns and rows that must be consistently the same height. The solution of this problem provided an overall offset for each of the 3×3 groups. The final result is a mesh where the height of each pixel indicates the shift between its wavelength response and that of the upper left most pixel on the camera. There are two key advantages to this technique. First, only local waveforms are ever correlated directly. This is important because the wavelength response drifts in overall shape across the sensor surface due to inhomogeneous illumination and curvature of the mirror structure. Comparing only local pixels, we are more assured that the resonant waveform has the same shape and its only the shift we are measuring. Secondly, by comparing each pixel to 8 of its neighbors, redundancy is gained which is used to improve the accuracy of the observed shift over a correlation done between just two pixels.

Interpreting the results: The four boxes of FIG. 10E in the mesh reflect the results. The boxes appear to be approximately 10 steps high. The steps indicated on the z-axis correspond to the 0.01 nm steps in wavelength that were taken.

The best sensitivity we could attain by including the extra SiO2 layer would be a 2/m shift in wavelength for a corresponding shift in surface height where m is the mode number given by m=2*d/lambda, lambda being the wavelength and d being the cavity size. For a 100 μm cavity and wavelengths in the neighborhood of 1.55 μm, the sensitivity would be 0.0155 nm shift in wavelength response for a 1 nm shift in sensor surface height. Alternatively stated, every 1 nm shift in wavelength indicates a 65 nm (1/0.0155) shift in sensor surface height. Again, this assumes a quarter-wavelength of SiO2 on the reflector surface. As this SiO2 layer would differ towards a half wave thickness, or zero thickness, the sensitivity would fall to 0.

With this in mind, we see that the 10 steps for the features in the mesh surface plot indicates a 0.1 nm shift in wavelength, which indicates a 6.5 nm step in the sensor surface. The target height of the features was 15 nm.

Figure 10A:
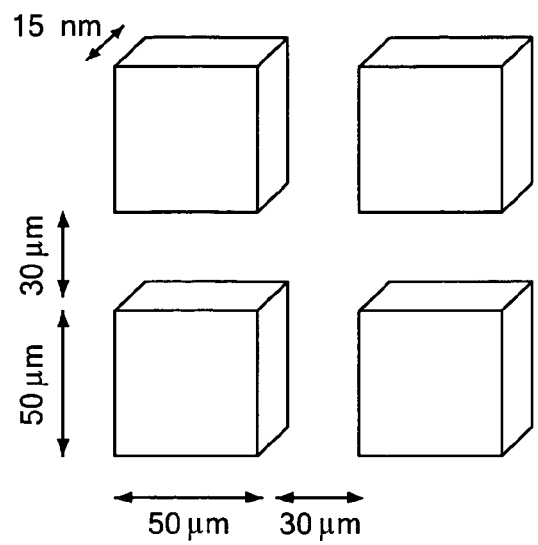
FIGS. 10A through 10E illustrate and example of the invention in actual test use.
Figure 10B:
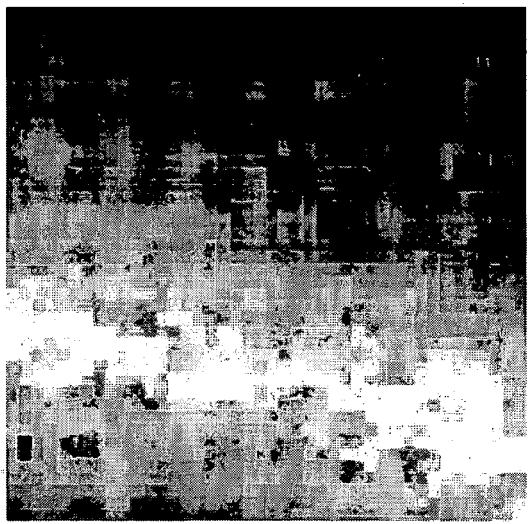
Figure 10C:
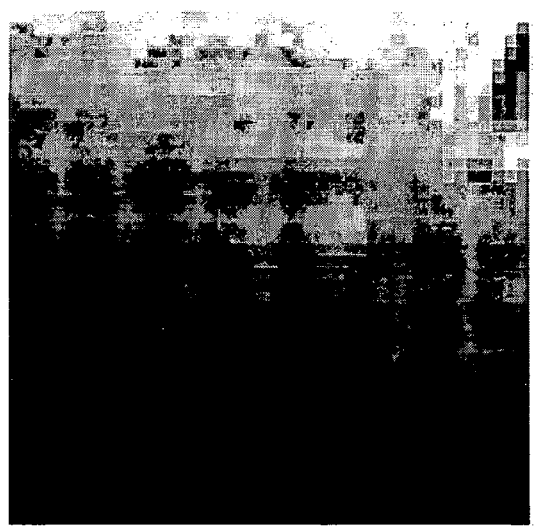

In FIG. 10A:
Model of SiO2 pattern created by photolithography and wet HF etch.
Surface sits on top of quarter wavelength layer of SiO2 (270 nm) for maximized sensitivity.

In FIGS. 10B and C:
View from camera at one fixed wavelength (lambda=1559.70 nm). Approximately 6× magnification so that each pixel represents approximately 10 microns square.
At most wavelengths the image is completely dark, and at a few, its nearly all bright. Here, at lambda=1559.70 nm, most of the surface is on its way to resonance (bright), but the 4 apparent squares in the upper right are lagging because of their shifted response.

Figure 10D:
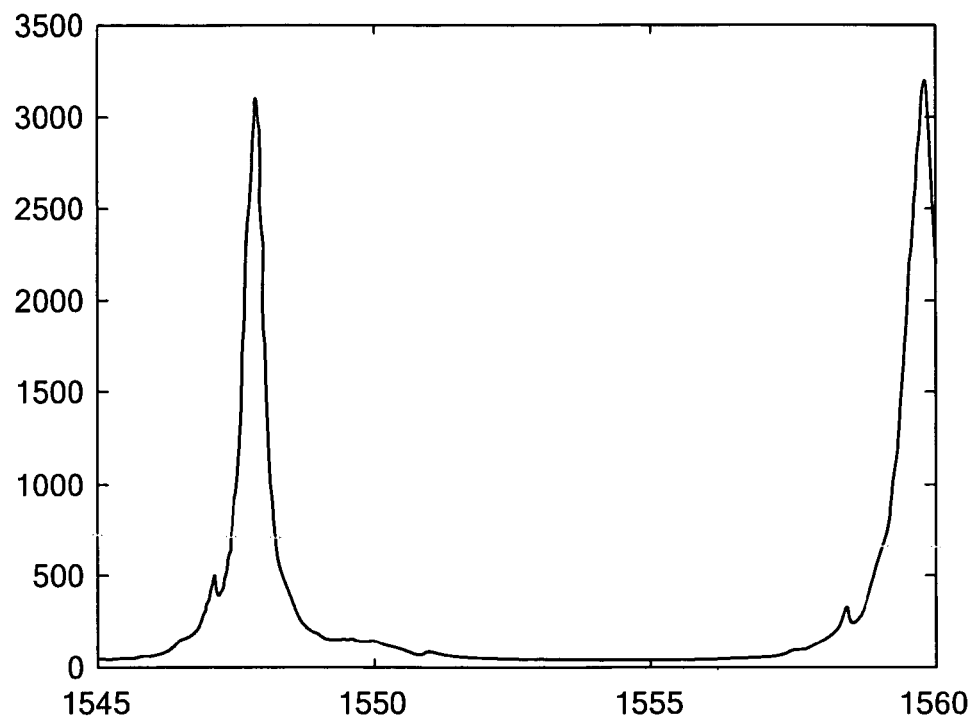
Figure 10E:
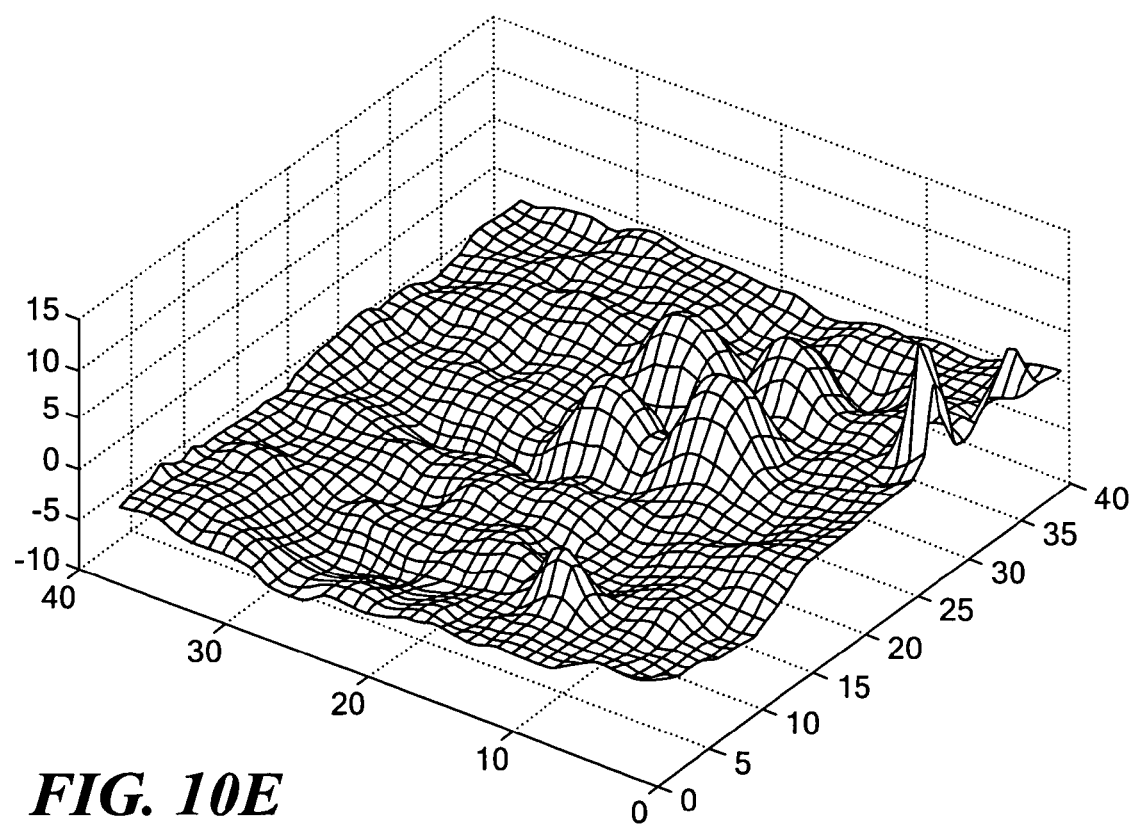

In FIG. 10D:
Bottom axis shows wavelength in nanometers. Vertical axis indicates relative intensity as measured by camera pixel. Previous image was taken at 1559.70 nm where we can see that the intensity was on the rise at this pixel, but not maximum. On the transition, the contrast is maximized and one is able to discern the 4 square features.

Here is the final mesh of shift vs. pixel position. The horizontal axes indicate pixel (this is a 40×40 section taken from the 128×128 array for clarity). The vertical axis indicates by how many steps the response was shifted relative to the bottom most corner pixel which was designated as having a 0 shift. The data was taken in steps of lambda=0.01 nm, so that the features, which appear to be 10 steps high, corresponds to a 0.1 nm shift in wavelength for their response. For this 100 μm cavity, every nanometer shift in resonant response indicates a 65 nm shift, so that these features would appear to be 6.5 nm in height.

Finally, the processing while still substantially real time may involve other or alternative mathematical techniques such as averaging, differentiating, integrating, curve fitting (in lieu of correlating), or correlating or otherwise comparing various frames or pixels of the multi-channel detector.

Figure 11:
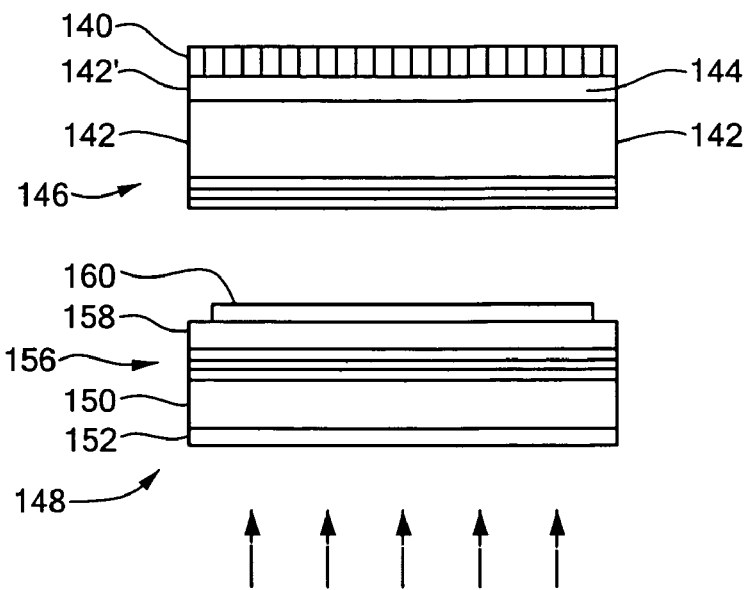
FIG. 11 illustrates an embodiment with an integral photodetector.

FIG. 11 illustrates an embodiment where the photodetector is provided on the exit mirror as an array 140 on a substrate 142, which may be silicon. Here as throughout the optical path an anti-reflective coating 144 is provided between them. Dialectric layers 146 are at the bottom of the substrate to provide the reflectivity described above. The bottom reflector structure 148 as above comprises a substrate 150, bottom coating 152 anti-reflective to the incident collimated beam 154. The substrate 150 has dielectric layers 156 and a silicon dioxide layer 158 on which the array of capturing material 160 is placed.

Figure 12:
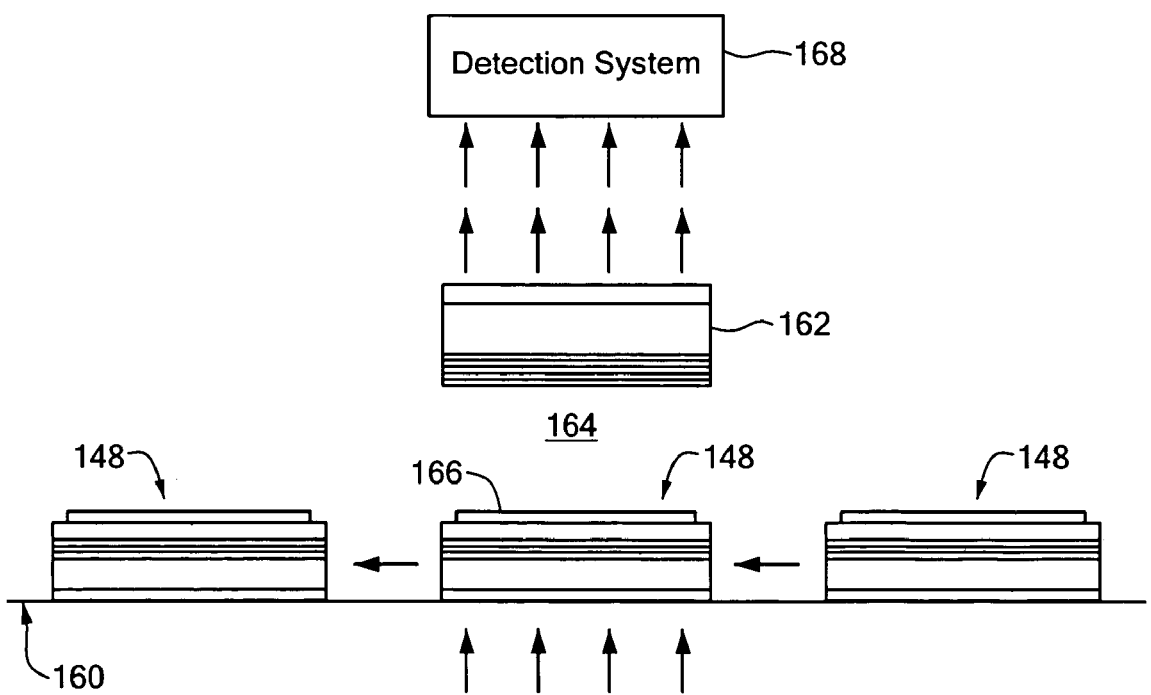
FIG. 12 illustrates a system for testing multiple arrays on a continuous basis.

FIG. 12 is an embodiment where plural testing units such as the bottom reflector structure 148 are passed under the upper reflector structure 162 of the type described above on a conveyor system 160. The light from the upper structure 162 after passing through the cavity 164 test material and capturing material 166 is received at a detection system 168 which may be as described above.

The invention described herein is to be limited only in accordance with the following claims:

What is claimed is:

1. An assay system comprising:
   first and second reflective surfaces that are structured and arranged to provide a channel therebetween, to accommodate a fluid having material to be tested, at least one of the first and second reflective surfaces having capturing material disposed in an array pattern, the array pattern having a plurality of resonant cavity regions between said first and second reflective surfaces;
   a source of radiation to illuminate each cavity region at a wavelength adapted to provide a standing wave of radiation within each said cavity region;
   a radiation detector that is structured and arranged to detect a change in a standing wave pattern, which is indicative of binding of the capturing material with the material to be tested in the fluid within each said cavity region; and
   means for dynamically varying spacing of said first and second surfaces.

2. An assay system comprising:
   first and second reflective surfaces that are structured and arranged to provide a channel therebetween, to accommodate a fluid having material to be tested;
   a plurality of regions in a pattern of an array between said first and surfaces, each region defining a cavity and having a capturing material on one of the first and second surfaces therein;
   a source of wavelength scanned radiation to illuminate each region at a wavelength adapted to provide a transmission of that radiation within each said cavity representative of material from said fluid bound to said capturing material;
   a detector for the transmitted radiation in each said cavity and operative to indicate a level of binding by said capturing material to said material to be tested in said fluid within each said cavity; and
   means for dynamically varying spacing of said first and second surfaces.

3. The assay system of claim 1 wherein said first and second reflective surfaces include one or more dielectric layers forming said corresponding reflective surface at a wavelength corresponding to said standing wave pattern.

4. The assay system of claim 1 wherein said capturing material as applied to each cavity forms a DNA or protein chip where individual capturing materials in each cavity are DNA or protein selective.

5. The assay system of claim 1 wherein said radiation source is an IR source.

6. The assay system of claim 1 wherein said radiation source is a laser source.

7. The assay system of claim 1 wherein said radiation source is a tunable laser source.

8. The assay system of claim 6 further including means for scanning said tunable laser through a range of wavelengths including a wavelength corresponding to said standing wave pattern in each cavity.

9. The assay system of claim 1 further including a beam expander in a path of radiation between said radiation source and said channel.

10. The assay system of claim 1 further including a beam condenser in a path of radiation between said channel and said detector.

11. The assay system of claim 1 wherein said detector includes a multi element detector wherein each element receives radiation from a corresponding cavity.

12. The assay system of claim 1 wherein said detector is a CCD detector.

13. The assay system of claim 1 wherein said first and said second reflective surfaces are parallel and radiation from said source is applied othogonally to said first and second reflective surfaces.

14. The assay system of claim 1 wherein said radiation is applied obliquely to at least one of said first and second surfaces.

15. The assay system of claim 1 wherein said detector detects one or more of radiation amplitude, phase, polarization and wavelength.

16. The assay system of claim 1 wherein said source of radiation includes means for causing said radiation to emit at discrete different wavelengths.

17. The assay system of claim 1 further including means for controlling a temperature of the fluid within said channel.

18. The assay system of claim 1 wherein said detection system includes a photodetector array integral with a support for one of said reflective surfaces which is not supporting a capturing material.

19. The assay system of claim 1 wherein said at least one reflective surface having said capturing material thereon has an added dielectric layer to provide a peak in a standing wave pattern in said cavity at said capturing material.

20. The assay system of claim 1 further including means for varying the spacing of said reflective surfaces to vary the cavity resonance condition.

21. A method for assaying a material under test, the method comprising:
   providing a channel bounded by first and second reflective surfaces adapted to accommodate at least one of the material under test and a fluid containing the material under test therebetween;
   providing a plurality of regions to one of said first and second reflective surfaces in an array of capturing material elements to form a corresponding plurality of resonant cavities;
   applying a capturing material to the capturing material elements in the array on one of the first and second surfaces;
   dynamically varying a spacing between said first and second reflective surfaces, to maintain said reflective surfaces in parallel throughout the method;
   passing the material under test or flowing the fluid containing the material through the channel;
   applying radiation as the fluid flows past or the material under test passes each region to illuminate each region at a wavelength adapted to provide a standing wave of radiation within each said resonant cavity; and
   measuring the radiation in each said resonant cavity; and detecting a change in resonant properties of the standing wave pattern, which is indicative of binding of the material under test to the capturing material at each said resonant cavity.

22. A method for assaying a material under test, the method comprising:
providing a channel bounded by first and second reflective surfaces adapted to accommodate at least one of the material under test and a fluid containing the material under test therebetween;
providing a plurality of regions to one of said first and second reflective surfaces in an array of capturing material elements between said first and second reflective surfaces;
applying a capturing material to the capturing material elements;
dynamically varying a spacing between said first and second reflective surfaces, to maintain said reflective surfaces in parallel throughout the method;
passing the material under test or flowing the fluid containing the material through the channel;
applying radiation as the fluid flows past or the material under test passes each region to illuminate each region at a wavelength adapted to provide a standing wave of radiation within each said resonant cavity; and
measuring the radiation in each said resonant cavity; and
detecting a change in resonant properties of the standing wave pattern, which is indicative of binding of the material under test to the capturing material at each said resonant cavity.

23. The assay method of claim 21 wherein said first and second reflective surfaces include one or more dielectric layers forming said reflective surface at a wavelength corresponding to said standing wave pattern.

24. The assay method of claim 23 further comprising:
applying said capturing material to each cavity in a DNA chip or protein chip format such that individual capturing materials in each resonant cavity are DNA or protein selective.

25. The assay method of claim 23 wherein said radiation is IR.

26. The assay method of claim 23 wherein said radiation is laser radiation.

27. The assay method of claim 23 including the step of tuning said radiation.

28. The assay method of claim 27 further including the step of scanning said radiation through a range of wavelengths including a wavelength corresponding to said standing wave pattern in each cavity.

29. The assay method of claim 23 further including the step of expanding said radiation in a beam along a path of radiation between said radiation source and said channel.

30. The assay method of claim 23 further including the step of condensing a beam of radiation along a path of radiation between said channel and said detector.

31. The assay method of claim 23 wherein said detecting step includes detecting in each of a plurality of detection elements wherein each element receives radiation from a corresponding cavity.

32. The assay method of claim 23 wherein said first and second surfaces are parallel and radiation from said source is applied othogonally to said first and second surfaces.

33. The assay method of claim 23 wherein said radiation is applied obliquely to at least one of said first and second surfaces.

34. The assay method of claim 23 wherein said detection step detects one or more of radiation amplitude, phase, polarization and wavelength.

35. The assay method of claim 23 wherein said radiation is emitted at discrete, different wavelengths.

36. The assay method of claim 23 further including the step of controlling a temperature of the fluid within said channel.

37. The assaying method of claim 23 wherein said detecting step includes detecting at a photodetector array integral with a support for one of said reflective surfaces which is not supporting a capturing material.

38. The assaying method of claim 23 wherein said reflective surface is provided having said capturing material thereon has an added dielectric layer to provide a peak in a standing wave pattern in said cavity at said capturing material.

39. The assay system of claim 23 further including varying the spacing of said reflective surfaces to vary the cavity resonance conditions.

40. An assay system comprising:
first and second reflective surfaces that are structured and arranged to define a space therebetween, the space being adapted to accommodate therebetween a material to be tested;
a plurality of regions in a pattern of an array between said first and said second reflective surfaces, each region defining a resonant cavity between the first and second reflective surfaces therein and having capturing material on at least one reflective surface;
a source of radiation to illuminate each region at a wavelength adapted to provide a standing wave of radiation within each said resonant cavity;
a detector for the radiation in each said resonant cavity and operative to indicate a change in the standing wave pattern, which is reflective of the binding of said material to be tested to the capturing material within each said resonant cavity; and
means for dynamically varying spacing of said first and second reflective surfaces.

41. An assay system comprising:
first and second reflective surfaces that are structured and arranged to define a channel therebetween, the channel being adapted to accommodate a material to be tested;
a plurality of regions in a pattern of an array between said first and said second reflective surfaces, each region defining a resonant cavity between the first and second reflective surfaces therein and having capturing material on at least one reflective surface;
a source of wavelength scanned radiation to illuminate each region at a wavelength adapted to provide a transmission of that radiation within each said resonant cavity representative of said material to be tested bound to the capturing material in each resonant cavity;
a detector for the radiation in each said resonant cavity and operative to indicate a level of binding of the capturing material to the material to be tested within each said resonant cavity; and
means for dynamically varying spacing of said first and second reflective surfaces.

* * * * *

UNITED STATES PATENT AND TRADEMARK OFFICE
CERTIFICATE OF CORRECTION

| | | |
|---|---|---|
| PATENT NO. | : 7,695,680 B2 | |
| APPLICATION NO. | : 10/549991 | |
| DATED | : April 13, 2010 | |
| INVENTOR(S) | : M. Selim Unlu et al. | |

It is certified that error appears in the above-identified patent and that said Letters Patent is hereby corrected as shown below:

Column 9, claim 2, line 39, "first and surfaces," should read --first and second surfaces,--.

Signed and Sealed this
Twenty-first Day of February, 2012

David J. Kappos
*Director of the United States Patent and Trademark Office*